United States Patent [19]

Dinella et al.

[11] Patent Number: 5,501,777
[45] Date of Patent: Mar. 26, 1996

[54] METHOD FOR TESTING SOLDER MASK MATERIAL

[75] Inventors: Donald Dinella, Berkeley Heights; Sudarshan Lal, Glen Rock, both of N.J.; Kim L. Morton, Richmond, Va.; David A. Nicol, Trenton, N.J.

[73] Assignee: AT&T Corp., Murray Hill, N.J.

[21] Appl. No.: 366,539

[22] Filed: Dec. 30, 1994

[51] Int. Cl.⁶ .............................. G01N 27/26; B05D 3/10
[52] U.S. Cl. ........................ 205/791; 204/400; 204/434; 427/304; 427/305
[58] Field of Search ................................. 204/153.1, 400, 204/434; 427/304, 305, 306

[56] References Cited

U.S. PATENT DOCUMENTS

| | | | |
|---|---|---|---|
| 3,223,598 | 12/1965 | Jacky et al. | 204/153.1 |
| 3,408,270 | 10/1968 | Gentile | 204/153.1 |
| 3,770,593 | 10/1973 | Dick | 204/153.1 |
| 4,541,902 | 9/1985 | Kinoshita et al. | 427/305 |
| 4,654,126 | 3/1987 | Amelio et al. | 204/434 |

Primary Examiner—T. Tung
Attorney, Agent, or Firm—Lester H. Birnbaum

[57] ABSTRACT

Disclosed is a method for testing solder mask material for suitability with an electroless plating process. The Emix potential of the electroless bath is measured. A test substrate including the mask material is then immersed in an electrolyte, and a constant potential at least equal to the Emix potential is applied to a pair of electrodes also immersed in the electrolyte. The test substrate is then inspected to determine adherence of the mask material.

7 Claims, 1 Drawing Sheet

METHOD FOR TESTING SOLDER MASK MATERIAL

BACKGROUND OF THE INVENTION

This invention relates to electroless plating operations and, in particular, to testing the suitability of material for such operations.

Electroless copper plating is an important step in the fabrication of printed circuit boards. Typically, pan of the fabrication sequence involves depositing a solder mask material over the board which includes copper pads and leads on one or more major surfaces, and leaving the pads exposed for later soldering. The exposed copper is then electrolessly plated to achieve the full thickness of any via holes and adjust plating heights to solder mask planarity.

One of the problems which can occur is "encroachment" where the solder mask lifts up during plating resulting in poorly adhered solder mask. Plating cycles are typically of the order of 12 hours and often provide inconclusive results for determining whether a particular solder mask material is unsuitable. Thus, it is desirable to have a quick method for determining whether a mask material will adhere to the board and metal layers during an electroless plating process.

SUMMARY OF THE INVENTION

The invention is a method for testing the adhesion of a mask material to an underlying substrate during an electroless plating process employing a particular bath. The electrical potential at which equal oxidation and reduction reactions occur in the bath is determined. The mask is deposited on a test substrate including conductive material on at least one major surface. The test substrate is then inserted into an electrolyte along with a pair of electrodes. A dc voltage at least equal to the determined electrical potential is applied to the electrodes. The test substrate is then examined to determine if any loss of adhesion occurs between the mask and substrate.

BRIEF DESCRIPTION OF THE DRAWING

These and other features of the invention are delineated in detail in the description to follow. In the drawing.

It will be appreciated that, for purposes of illustration, these figures are not necessarily drawn to scale.

DETAILED DESCRIPTION OF THE INVENTION

Figure 1:
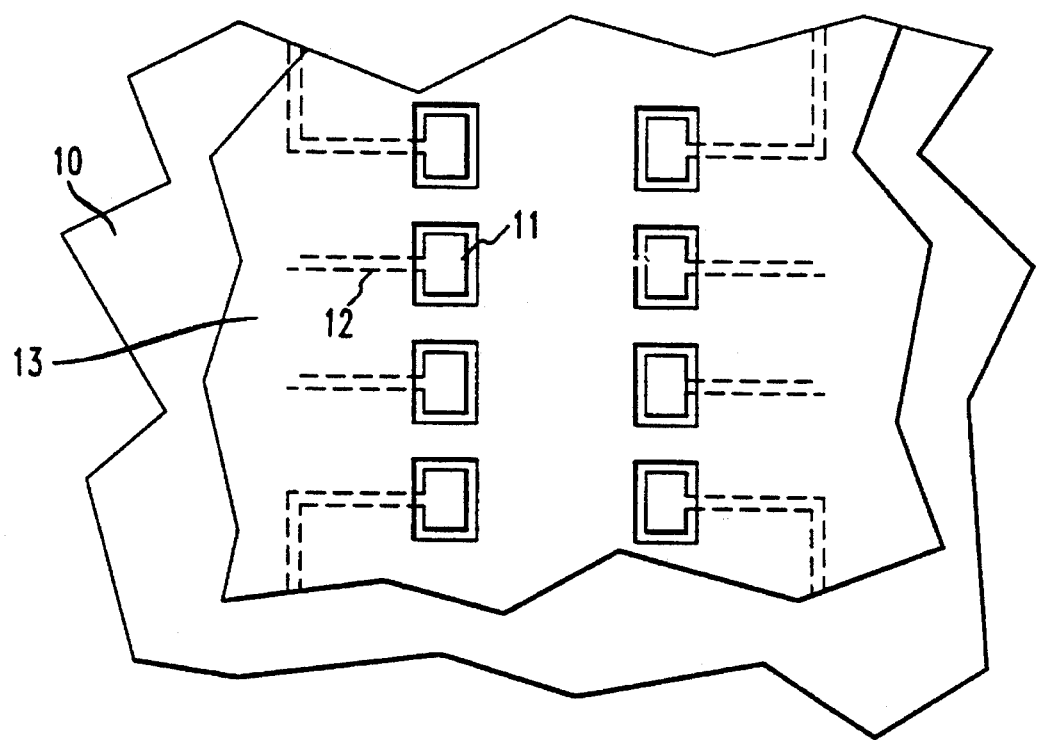
FIG. 1 is a plan view of a portion of a test pattern in accordance with an embodiment of the invention.

FIG. 1 illustrates a portion of a typical test substrate which may be used in accordance with the invention. The substrate, 10, is a standard printed circuit board material such as epoxy glass. Deposited on at least one major surface of the substrate are conductive patterns which typically include bonding pads, e.g., 11, and leads, e.g., 12, extending therefrom. The conductive patterns are typically made from copper which is deposited by plating to a thickness of approximately 25 microns.

Formed over essentially the entire surface of the substrate, 10, except for the area of the exposed pads, e.g., 11, is the solder mask, 13, to be tested. The mask is deposited by standard means such as curtain coating, screening or spraying, and patterned according to known photolithographic techniques. The thickness of the mask, 13, is typically approximately 50 microns.

The test is designed to provide a quick indication of how well the solder mask will adhere when it is subjected to the electroless plating operation. In this example, the electroless plating bath is a standard copper electroless bath comprising a source of copper such as copper oxide, a reducing agent such as formaldehyde, a complexing agent such as ethylene diamine tetraacetic acid (EDTA), and sodium hydroxide. The invention may be used with other electroless baths.

Figure 2:
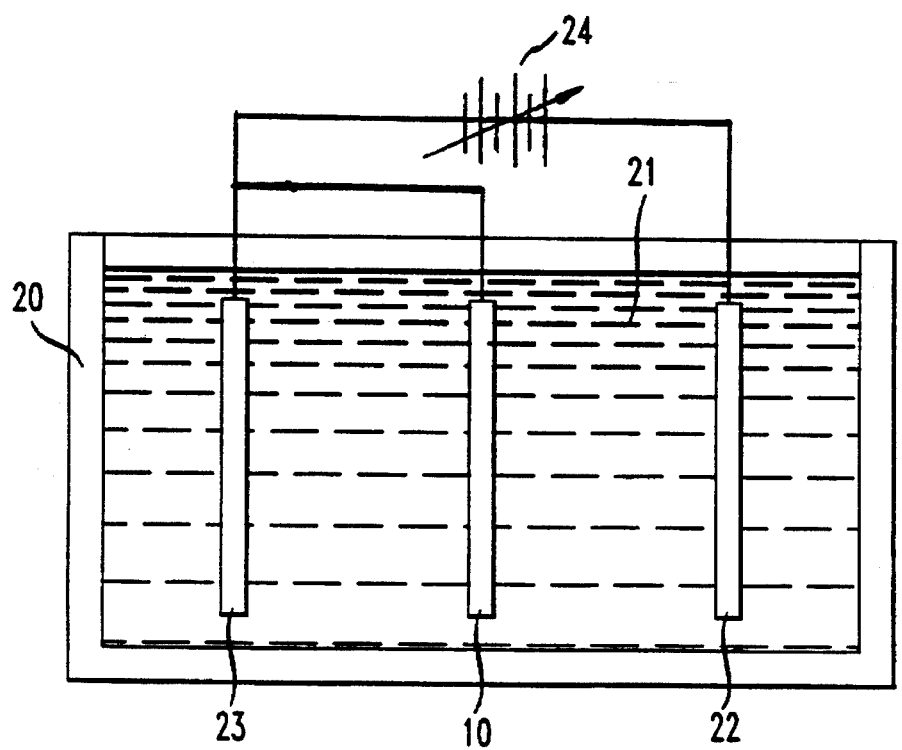
FIG. 2 is a schematic illustration of an apparatus which may be used in accordance with an embodiment of the invention.

In order to test the solder mask, the test substrate, 10, with the solder mask, 13, thereon was immersed in a container, 20, as illustrated in FIG. 2. The container included an electrolyte solution, 21. In this example, the solution comprised 2 percent sodium formate and 98 percent water. However, other electrolyte solutions may also be used. Also immersed in the electrolyte were a pair of electrodes, 22 and 23. Electrode 22, in this example, was a silver metal coated with silver chloride, while electrode 23 was made of platinum.

A source of dc potential, 24, such as a potentiostat, was applied to the electrodes so that a positive potential was applied to electrode 22, while a negative potential was applied to both the test substrate, 10, and to the other electrode, 23. Electrode 22, therefore, served as a reference electrode, while electrode 23 served as a cathode.

The magnitude of the constant dc potential applied to the electrodes and test substrate was at least equal to the Emix potential of the electroless plating bath. As known in the art, the Emix potential is the potential at the surface of a substrate during an electroless plating when the oxidation and reduction reactions are equal. This potential can be determined by any number of known techniques. In this example, the Emix potential was measured by applying a voltmeter to a substrate and a reference electrode during electroless plating. The potential for the bath employed in this example was −800 mV.

When a potential equal to the Emix potential of the bath was applied to the apparatus of FIG. 2 while the electrolyte was held at approximately 60 degrees C., it was discovered that the electrolyte simulated the effect of the electroless process on the mask, but at a much accelerated rate. Thus, in this example, after only 3 hours, the test substrate was removed from the electrolyte and visually inspected in an area of the copper pads, e.g., 11, to see if the solder mask maintained its adherence to the underlying substrate and metallization. The amount of lift-off, if any, was found to be the same as that which would occur if the mask had been subject to a 12 hour cycle in the electroless bath. In general, it is expected that the test substrate will be immersed in the electrolyte for a period in the range 2 to 4 hours.

It was also discovered that increasing the voltage increased the amount of lift-off of the mask material. Consequently, a potential greater than the Emix potential can be applied. However, the upper limit on applied potential should be approximately 1000 mV.

In general it is desired to keep the temperature of the electrolyte, 21, at the same temperature as the plating bath. Consequently, a temperature in the range 55–65 degrees C. is desirable.

While the invention has been described with regard to a solder mask material, it will be appreciated that the invention is also applicable for testing the adhesion of other types of masks such as standard photoresist masks.

We claim:

1. A method for testing the adhesion of a mask material to an underlying substrate during an electroless plating process employing a particular bath comprising the steps of:

determining the electrical potential at a surface of the substrate at which equal oxidation and reduction reactions occur in the bath;

depositing the mask material on a surface of a test substrate, which surface includes conductive material;

immersing the test substrate in an electrolyte along with a pair of electrodes;

applying to the electrodes a dc potential at least equal to the determined electrical potential such that the test substrate is a cathode; and examining the test substrate to determine if any loss of adhesion occurs between the mask and the substrate.

2. The method according to claim 1 wherein the electrolyte comprises sodium formate and water.

3. The method according to claim 1 wherein the conductive material is copper.

4. The method according to claim 3 wherein the bath comprises copper oxide, formaldehyde, ethylene diamine tetraacetic acid, and sodium hydroxide.

5. The method according to claim 1 wherein the test substrate is immersed for a period in the range 2 to 4 hours.

6. The method according to claim 1 wherein the test substrate is a printed circuit board.

7. The method according to claim 1 wherein the electrolyte is held at a temperature within the range 55 to 65 degrees C.

* * * * *